United States Patent
Dijksman et al.

(10) Patent No.: US 9,550,050 B2
(45) Date of Patent: Jan. 24, 2017

(54) MEDICAMENT DELIVERY APPARATUS

(75) Inventors: Johan Frederik Dijksman, Weert (NL); Anke Pierik, Eindhoven (NL); Judith Margreet Rensen, Eindhoven (NL); Jeff Shimizu, Cortlandt Manor, NY (US); Hans Zou, Windsor, NJ (US); Michel Pardoel, Mierlo (NL); Frits Tobi De Jongh, Beek en Donk (NL)

(73) Assignee: Medimetrics Personalized Drug Delivery B.V., Eindhoven (NL)

( * ) Notice: Subject to any disclaimer, the term of this patent is extended or adjusted under 35 U.S.C. 154(b) by 962 days.

(21) Appl. No.: 12/442,408

(22) PCT Filed: Sep. 20, 2007

(86) PCT No.: PCT/IB2007/053826
§ 371 (c)(1),
(2), (4) Date: Nov. 3, 2009

(87) PCT Pub. No.: WO2008/038199
PCT Pub. Date: Apr. 3, 2008

(65) Prior Publication Data
US 2010/0063486 A1    Mar. 11, 2010

Related U.S. Application Data

(60) Provisional application No. 60/826,838, filed on Sep. 25, 2006.

(51) Int. Cl.
*A61K 9/22* (2006.01)
*A61M 31/00* (2006.01)
(Continued)

(52) U.S. Cl.
CPC ........... *A61M 31/002* (2013.01); *A61M 31/00* (2013.01); *A61B 5/073* (2013.01); *A61B 5/4839* (2013.01)

(58) Field of Classification Search
CPC ................ A61M 31/002; A61M 5/172; A61M 2210/1042; A61M 2205/3523; A61M 31/00; A61M 25/00
(Continued)

(56) References Cited

U.S. PATENT DOCUMENTS 4,239,040 A * 12/1980 Hosoya ............... A61M 31/002
600/582
5,279,607 A   1/1994 Schentag
(Continued)

FOREIGN PATENT DOCUMENTS

EP    1669026 A1    6/2006
JP    430534    3/1992
(Continued)

OTHER PUBLICATIONS

The European Office Action mailed Sep. 16, 2013 for European patent application No. 07826480.1, 4 pages.

*Primary Examiner* — Phillip Gray
(74) *Attorney, Agent, or Firm* — Lee & Hayes, PLLC

(57) ABSTRACT

An electronic capsule (100) is provided. The capsule (100) has a discrete drive element (300) comprising: a housing (109), electronics for making the electronic capsule (100) operable, a pumping mechanism (115) for dosing and displacing a substance, a power source (105) for powering the electronic capsule (100) and enabling the electronics and the pumping mechanism (115) to operate, and a locking mechanism (130); and a discrete payload element (200) comprising: a housing (109), a reservoir (210) for storing the substance, one or more openings (250) in the housing (109) for releasing the substance from the reservoir (210) and a locking mechanism (230) for engaging the drive element locking mechanism (130). Engagement of the drive element locking mechanism (130) with the payload element locking mechanism (230) secures the drive element (300) to the
(Continued)

payload element (200), thereby making the electronic capsule (100) operable and specific.

26 Claims, 5 Drawing Sheets

(51) Int. Cl.
 *A61B 5/07* (2006.01)
 *A61B 5/00* (2006.01)
(58) Field of Classification Search
 USPC .............. 604/890.1–892.1, 65–67, 151–155,
 132,604/133
 See application file for complete search history.

(56) References Cited

U.S. PATENT DOCUMENTS

| | | | |
|---|---|---|---|
| 5,785,688 A * | 7/1998 | Joshi | A61M 5/14593 604/132 |
| 5,879,322 A | 3/1999 | Lattin | |
| 5,911,716 A * | 6/1999 | Rake | A61M 5/148 128/DIG. 12 |
| 6,010,492 A | 1/2000 | Jacobsen | |
| 6,632,216 B2 | 10/2003 | Houzego | |
| 2003/0020810 A1 * | 1/2003 | Takizawa | A61B 1/00105 348/68 |
| 2003/0214579 A1 | 11/2003 | Iddan | |

FOREIGN PATENT DOCUMENTS

| | | |
|---|---|---|
| JP | 430535 | 3/1992 |
| JP | 2001122355 | 5/2001 |
| JP | 2001299910 | 10/2001 |
| JP | 2002523132 | 7/2002 |
| WO | 9605812 A1 | 2/1996 |
| WO | WO2005063111 | 7/2005 |
| WO | 2005105053 A2 | 11/2005 |
| WO | 2006021932 A1 | 3/2006 |
| WO | 2006025013 A1 | 3/2006 |
| WO | 2006077527 A2 | 7/2006 |
| WO | 2006077528 A2 | 7/2006 |
| WO | 2006077529 A2 | 7/2006 |
| WO | 2006077530 A2 | 7/2006 |
| WO | 2007057838 A1 | 5/2007 |
| WO | 2007148238 A1 | 12/2007 |
| WO | 2008012700 A1 | 1/2008 |
| WO | 2008017967 A1 | 2/2008 |

* cited by examiner

MEDICAMENT DELIVERY APPARATUS

RELATED REFERENCES

The present disclosure is related to U.S. Provisional Patent Application No. 60/644,540, entitled "Electronicially Controlled Capsule For Releasing Radiation", and filed Jan. 18, 2005, U.S. Provisional Patent Application No. 60/644,539, entitled "Electronicially Controlled Capsule", and filed Jan. 18, 2005, U.S. Provisional Patent Application No. 60/644,538, entitled "Electronicially Controlled Ingestible Capsule", and filed Jan. 18, 2005, U.S. Provisional Patent Application No. 60/644,518, entitled "System And Method For Controlling Traversal Of An Ingested Capsule", and filed Jan. 18, 2005, U.S. Provisional Patent Application No. 60/606,276, entitled "Electronically Controlled Pill And System For Delivering At Least One Medicament", and filed Sep. 1, 2004, U.S. Provisional Patent Application No. 60/605,364, entitled "Electronically And Remotely Controlled Pill And System For Delivering At Least One Medicament", and filed Aug. 27, 2004, U.S. Provisional Patent Application No. 60/738,238, entitled "System and Method for Interacting With a Cell or Tissue", and filed Nov. 18, 2005, U.S. Provisional Patent Application No. 60/805,223, entitled "Electronic Capsule And Method For Treating Gastrointestinal Disease", and filed Jun. 20, 2006, U.S. Provisional Patent Application No. 60/805,645, entitled "Medicament Delivery System And Process", and filed Jun. 23, 2006, and U.S. Provisional Patent Application No. 60/821,622, entitled "Device, System And Method for Interacting With A Cell Or Tissue In A Body", and filed Aug. 7, 2006, with each of the foregoing references being assigned to the Assignee of the present disclosure and hereby being expressly incorporated by reference as part hereof.

The present invention relates to an ingestible electronic capsule. More particularly, the present invention relates to an electronic capsule that has a discrete drive element and a discrete payload element wherein the electronic capsule becomes operable and specific when the drive element and the payload element are attached.

A continuing need for a non-invasive means for the precise delivery of medicaments to selected sites in the animal alimentary canal exists. Electronic capsules or pills are known. Electronic pills typically have a housing made from bio-compatible materials that houses both a medicament reservoir containing a pre-dosed amount of a medicament and control electronics for precisely delivering the medicament to a pre-selected site in the gastrointestinal tract of a human or animal. Also contained by the housing is a means for providing a link for wireless communication by the pill to the outside of the body upon ingestion of the pill by a subject. The electronics enable the pill to deliver the on board medicament at a specific site in the gastrointestinal tract of a human or animal using sensors, timing or location.

Electronic pills for delivering a medicament upon recognition of an electronic signal have had some success in delivery of medicament to a selected site. A recent example of an electronic pill is described in U.S. Pat. No. 6,632,216 to Houzego et al. Houzego is directed to an ingestible capsule for delivering a substance to the gastrointestinal tract of a mammal comprising an openable reservoir for the substance that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range, the receiver including an air core having coiled therearound a wire; characterized in that the coiled wire lies on or is embedded in an outer wall of the device.

Another electronic pill is described in U.S. Pat. No. 5,279,607 to Schentag, et al. Schentag is directed to an ingestible capsule and process for delivery, particularly repeatable delivery, of a medicament to the alimentary canal is disclosed wherein an essentially non-digestible capsule contains an electric energy emitting means, a radio signal transmitting means, a medicament storage means and a remote actuatable medicament releasing means. The capsule signals a remote receiver as it progresses through the alimentary tract in a previously mapped route and upon reaching a specified site is remotely triggered to release a dosage of medicament.

The Krill and Schentag disclosures are illustrative of known electronic pills or capsules. Known capsules house all capsule components therein. Such capsules fail to provide means for addressing the lifetime issues associated with diffent components of the capsule. Specifically, the medicament to be dispensed by the capsule has associated lifetime or shelf life issues and must be dispensed prior to an expiration date for optimal effectiveness. The electronic capsule power supply, typically a battery, also has lifetime issues associated therewith. An expired battery may render a capsule non-functional or unreliably functional. Thus, known electronic capsules contain both electronics and a medicament having differing and unrelated lifetime issues. Accordingly, electronic pills currently known in the art are limited by an inability to address these disparate lifetime issues.

Moreover, medicaments and power supplies typically have different storage requirements for appropriate storage. For example, medicaments and power supplies may have differing temperature and humidity requirements for storage. The Krill and Schentag disclosures further illustrate electronic capsules lacking means for appropriate storage solutions suitable for both the medicament to be dispensed by a capsule and the power supply housed therein.

A need therefore exists for an electronic capsule that decouples the lifetime issues of the medicament stored by the electronic capsule from the lifetime issues of the driver part, e.g. the battery and further decouples storage issues of the medicament part from the storage issues of the electronics part, thereby allowing appropriate storage in a variety of appropriate conditions relating to temperature, humidity, etc.

A need further exists for an electronic capsule having a general purpose electronic component and a separate and distinct medicament specific payload component, wherein the electronic capsule becomes specific and operable when the general purpose electronic component and the medicament specific payload component are attached.

It is an object of the present invention to provide a simple and convenient means for accurate and reliable delivery of a controlled quantity of a substance, such as a pharmaceutically active compound, foodstuff, dye, radio labeled marker, vaccine, physiological marker or diagnostic agent to a selected site in the alimentary canal of human or animal.

It is an object of the present invention to provide an electronic capsule that resolves storage and operational issues associated with the disparate shelf lives issues of the medication to be dispensed by the capsule and the power supply housed by the electronic capsule.

It is also an object of the invention to provide an electronic capsule that decouples the lifetime or freshness issues related to the shelf life of the medicament(s) contained by the capsule from the lifetime or freshness issues related to the power source that powers the capsule.

It is additionally an object of the invention to provide an electronic capsule having a separate and discrete general purpose electronic component.

It is a further object of the invention to provide an electronic capsule having a separate and discrete medicament specific payload component.

It is a still further object of the invention to provide an electronic capsule wherein the electronic capsule becomes specific and operable when the general purpose electronic component and the medicament specific payload component are attached.

It is yet another object of the invention to provide an electronic capsule that simplifies and economizes the manufacturing process.

These and other objects and advantages of the present invention are achieved by an electronic capsule comprising a discrete drive element comprising: a housing, electronics for making the electronic capsule operable, a communication means for enabling the electronic capsule to send and receive commands, a pumping mechanism for dosing and displacing a substance, a power source for powering the electronic capsule and enabling the electronics, the communication means and the pumping mechanism to operate, and a locking mechanism or connector; and a discrete payload element comprising: a housing, a reservoir for storing the substance, one or more openings in the housing for releasing the substance from the reservoir and a locking mechanism or connector for engaging the drive element locking mechanism, wherein engagement of the drive element locking mechanism with the payload element locking mechanism secures the drive element to the payload element, thereby making the electronic capsule operable and specific.

The foregoing and still other objects and advantages of the present invention will be more apparent from the following detailed explanation of the preferred embodiments of the invention in connection with the accompanying drawings.

Figure 5:
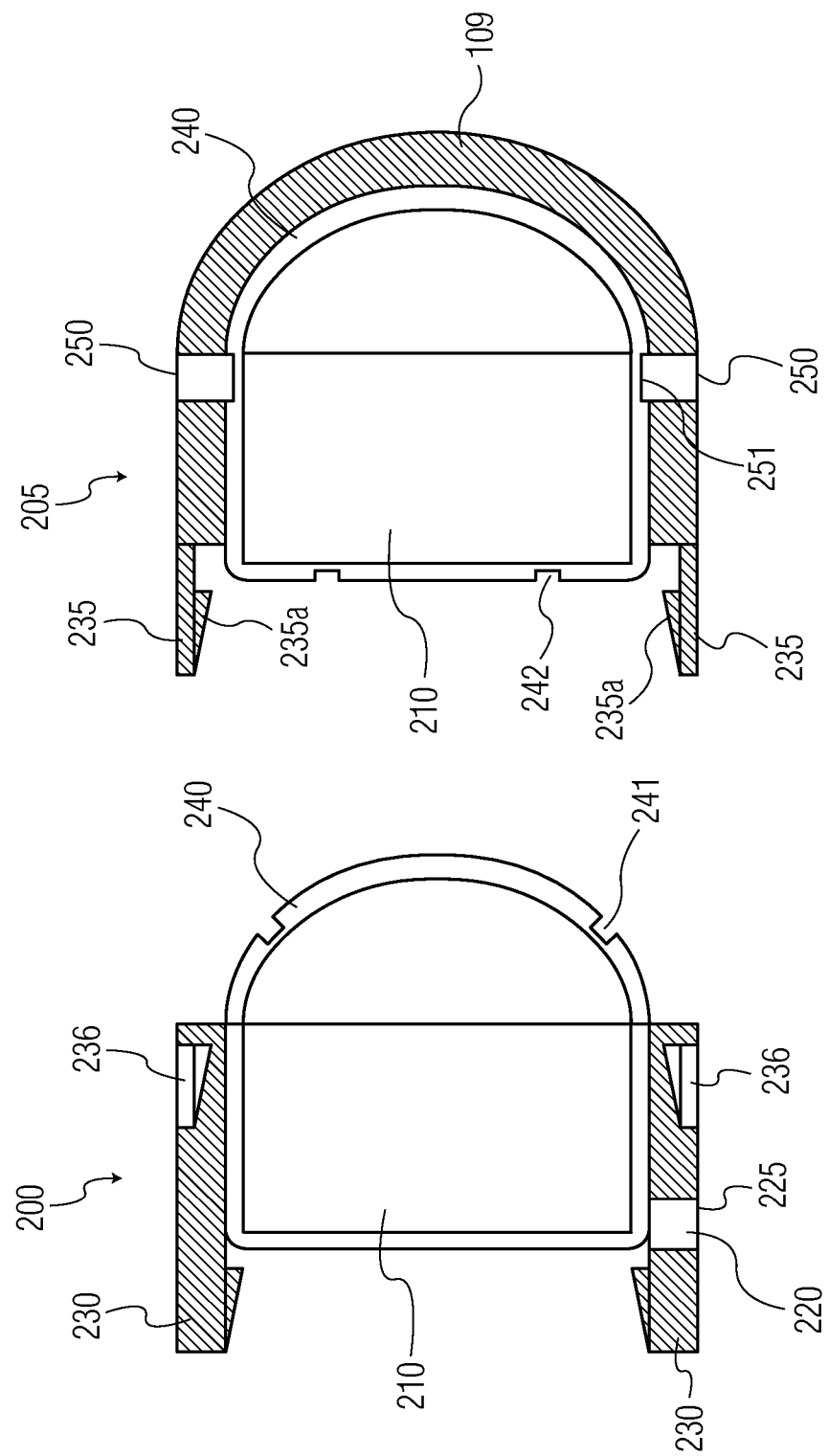
Figure 6:
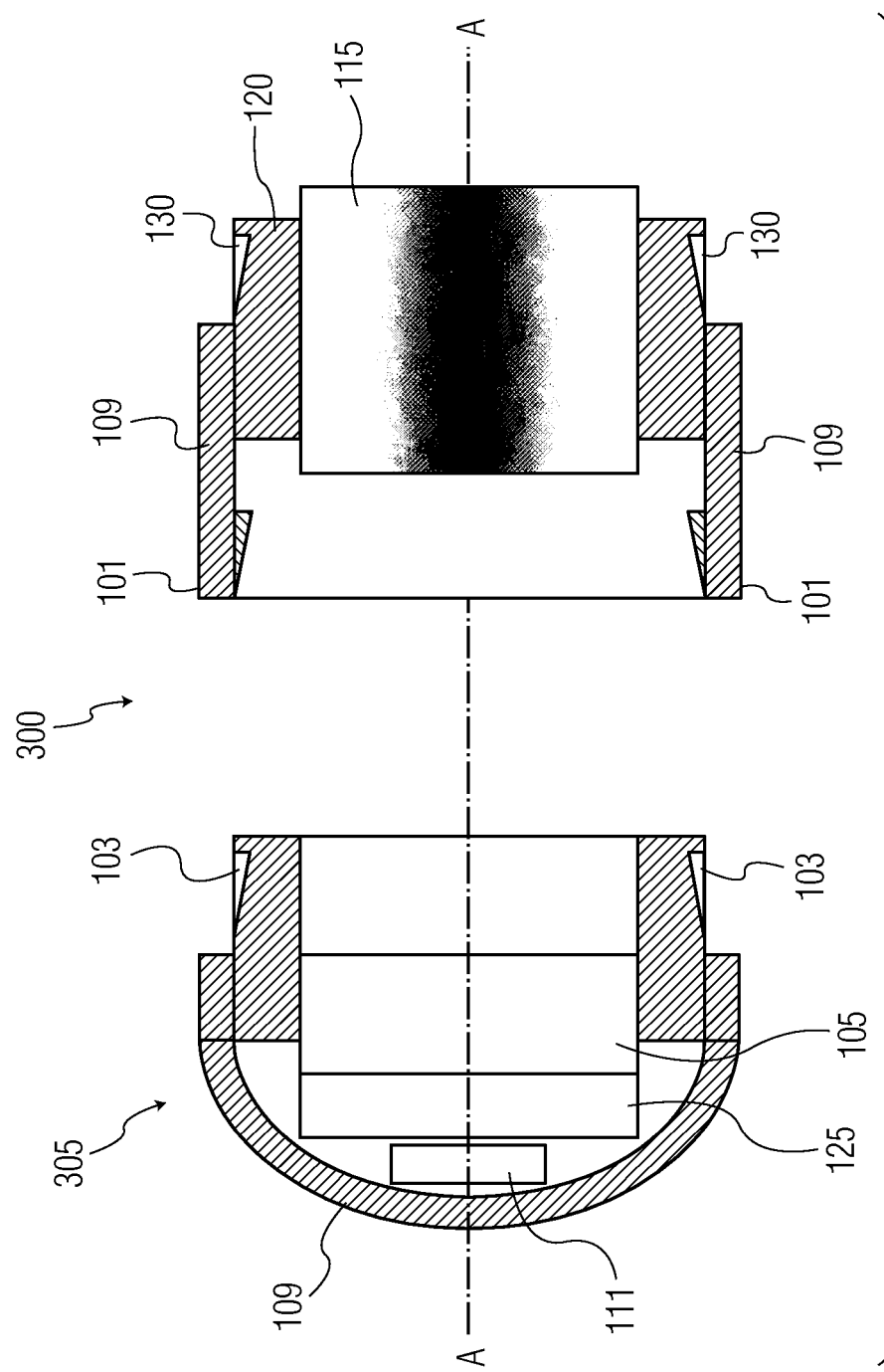

FIG. 5 is a schematic diagram showing a lateral cross-section of two discrete and attachable payload elements of an electronic capsule in accordance with a third embodiment of the present invention; and FIG. 6 is a schematic diagram showing a lateral cross-section of a drive element of an electronic capsule having a separate and attachable electronic power source and a separate and attachable electronic housing an in accordance with a fourth embodiment of the present invention.

An apparatus for dosing medications in a controlled way by delivering a substance to a selected site in the alimentary canal of a subject human or animal is provided. Specifically, an ingestible electronic pill or capsule having separate and attachable elements is provided. As used herein and in the claims the words "substance" and "payload" refer to medicines, non-medicinal substances, contrast agents, gases, fluids, liquids, chemicals, radiological agents, imaging markers, sensors for monitoring vitals, etc.

Figure 1:
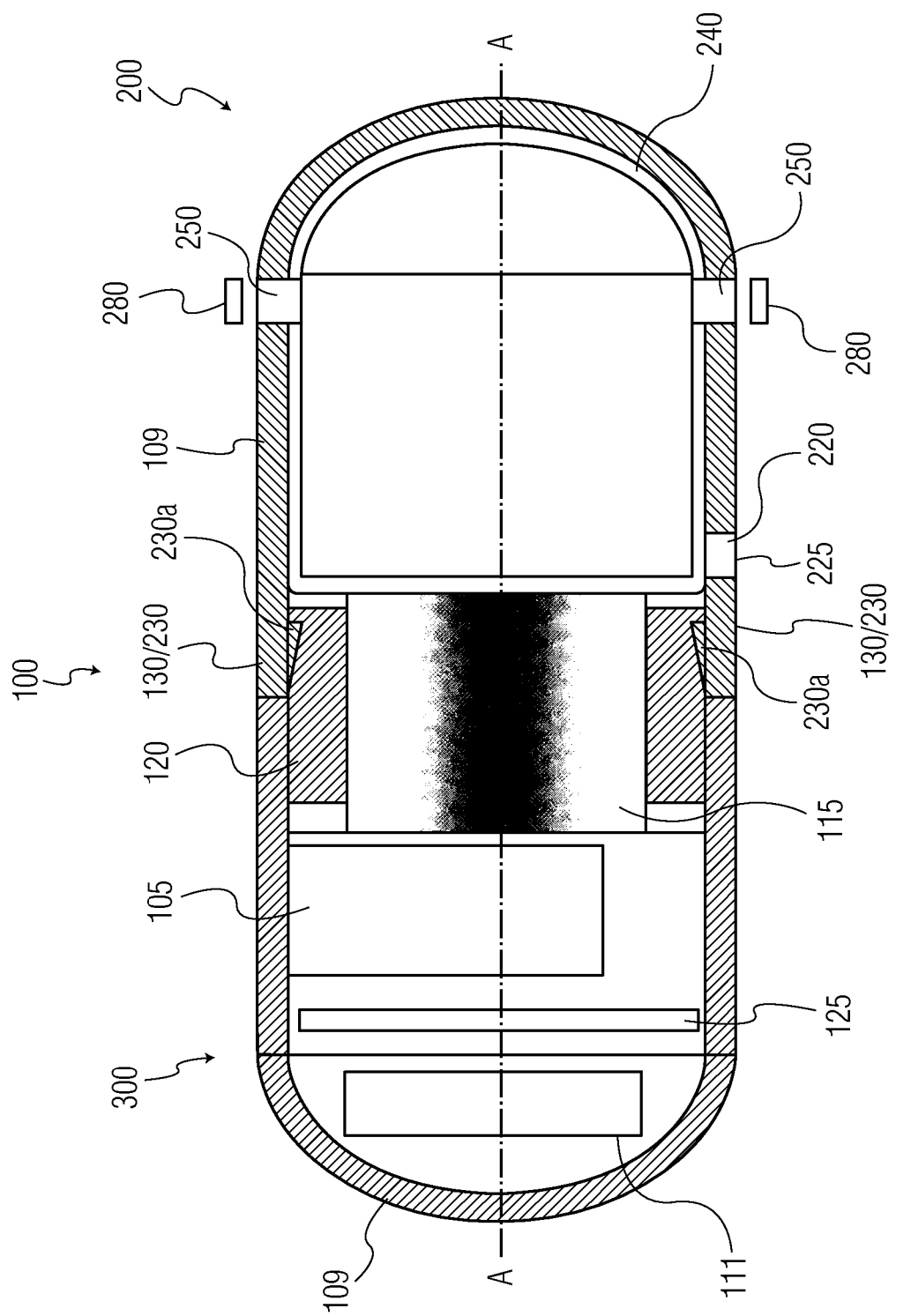
FIG. 1 is a schematic diagram showing a lateral cross-section of an assembled, operable electronic capsule in accordance with the present invention.

Referring to the drawings and, in particular, FIG. 1, there is illustrated an ingestible capsule according to the present invention generally represented by reference numeral 100. Capsule 100 is a self-contained, electronically controlled medicament delivery system for ingestion by a subject human or animal. As described in detail below, capsule 100 has a separate and distinct payload element 200 and a separate and distinct drive element 300. When payload element 200 and drive element 300 are attached, as illustrated, capsule 100 becomes operable and specific.

Payload element 200 and drive element 300 of capsule 100 have an outer shell or housing 109. Housing 109 is preferably made from bio-compatible materials such that capsule 100 is bio-compatible for at least the amount of time it requires to traverse the gastrointestinal tract of a human or animal. The bio-compatible materials are preferably stable at room temperature and below room temperature, such that capsule 100 has a long shelf life. Housing 109 may be fabricated from a biologically safe polymeric material such as, for example, polytetrafluoroethylene, polypropylene, polyethylene, acrylics and the like. Housing 109 is more preferably manufactured from materials used to fabricate implantable devices, including pacemaker leads and cardiac prosthesis devices, such as artificial hearts, heart valves, intra-aortic balloons, and ventricular assist devices. These materials include Pellethane® 2363 polyetherurethane series of materials available from Dow Chemical Company and Elasthane polyetherurethane available from the Polymer Technology Group, Inc. Other materials include PurSil® and CarboSil® also available from the Polymer Technology Group, Inc. Assembled capsule 100 is preferably sized to be suitable to be swallowed by a human or animal. Preferably, assembled capsule 100 is about 1 cm in diameter and 2 to 3 cm long.

Figure 2:
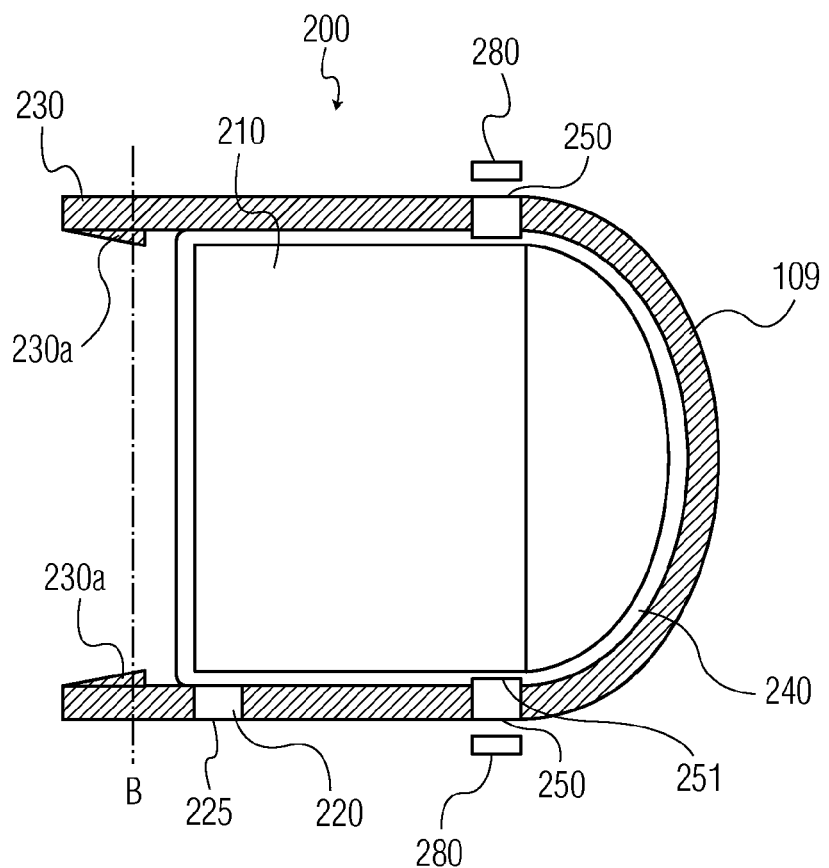
FIG. 2 is a schematic diagram showing a lateral cross-section of a payload element of an electronic capsule in accordance with the present invention.

Payload element 200 is illustrated in FIGS. 1 and 2. Payload element 200 houses a payload (not shown) in a reservoir 210. The payload is preferably a controlled quantity of a substance to be delivered to a selected site in a human or animal at a predetermined instant in time. Non-limiting examples of a suitable substance for use with the present invention include pharmaceutically active compounds, foodstuffs, dyes, radiolabelled markers, vaccines, physiological markers or diagnostic agents. Particularly, the substance may be a medically efficacious material such as, for example, antibiotics, antiviral compounds, chemotherapeutic agents, nutriments (e.g. vitamins, minerals, enzymes), radio isotopes, dyes, tracers, radio opaque materials, growth factors, hormones, steroids, and the like, or any combination thereof. The substance is preferably a medicament for treatment of diseases of the gastrointestinal tract. More preferably, the substance is a 5-ASA or a corticosteroid such as budesonide. The medicament can further be an oral contrast agent used to enhance diagnostic images. An example of such a contrast agent is Gastromark® for MRI images and Barium for CT images. The medicament to be dispensed by capsule 100 is preferably hermetically sealed in reservoir 210.

Payload element 200 has one or more openings 250 in housing 109 for enabling a medicament to be deposited in and dispensed from reservoir 210. Each opening 250 is sealed with a plug 280. Payload element 200 also has a gasketing insert 240 for providing a seal around reservoir 210. Gasketing insert 240 has weakened areas 241 and 242.

Payload element further has at least one vent opening 220 and at least one semi-permeable membrane 225. Vent opening 220 functions to balance pressure inside capsule 100 with pressure outside capsule 100. Semi-permeable membrane 225 overlies vent opening 220 and allows for air transport from the outside of capsule 100 to the inside of capsule 100 and vise versa, thereby preventing water or other fluid substances from penetrating the inside of the electronic pill. Specifically, semi permeable membrane 225 allows gasses to pass through vent opening 220 and prevents liquids from entering capsule 100. Preferably, semi-permeable membrane 225 is an integral and immovable part of housing 109. Payload element 200 further has a pair of connectors or locking mechanisms 230 disposed on housing 109.

Figure 3:
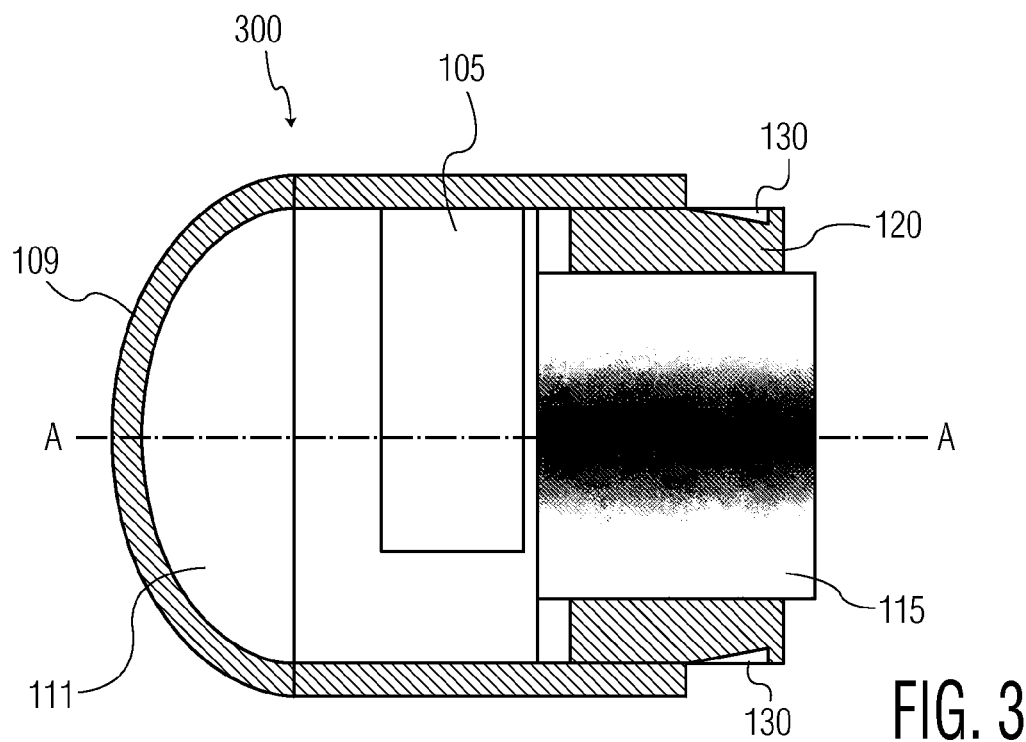
FIG. 3 is a schematic diagram showing a lateral cross-section of a drive element of an electronic capsule in accordance with the present invention.

Drive element 300 is illustrated in FIGS. 1 and 3. Drive element 300 houses the mechanical and electrical elements that make capsule 100 operable. Specifically, drive element 300 contains a pumping device or drive unit 115 for dosing and displacing a medicament housed in reservoir 210, an electrical motor support 120, a sensor platform 125, a power source 105 and an electronics housing 111. Dispense of the payload from reservoir 210 may also be achieved by osmotic means, by metered pumping mechanism means employing a mechanical or chemical pump, or by any other known means for achieving delivery of a substance.

Power source 105 powers the control circuitry in order for each of the mechanical and electrical components to operate. Power source 105 additionally powers any other electrically powered equipment housed by capsule 100. Power source 105 may be a battery, a capacitor or any other known means for providing a power supply.

Electronics housing 111 houses mechanical and electrical elements necessary for operation of capsule 100. The electrical elements housed by electronics housing 111 for communication and for controlling release of a medicament stored in reservoir 210 may include, without limitation, a drive unit for an electrical motor, sensors for aiding in determining the location of capsule 100 without physical contact, communication means such as, for example, an RF transceiver, an antenna, and a read-out device for sensor platform 125. Drive element 300 further has a pair of connectors or locking mechanisms 130 disposed in housing 109. Locking mechanisms 130 of drive element 300 interact with locking mechanisms 230 of payload element 200 to achieve stable and secure attachment of payload element 200 to drive element 300, thereby forming a specific and operable capsule 100.

Payload element 200 is mounted or attached to drive element 300 to form an operable capsule 100 by movement along a direction parallel to the axis A-A relative to the length of capsule 100, as illustrated in FIG. 1. According to a first embodiment of the present invention illustrated in FIGS. 1 to 3, locking mechanism pair 130 of drive element 300 is a pair of anchoring recesses 130 and locking mechanism pair 230 of payload element 200 is a pair of locking pins. Anchoring recesses 130 comprise two or more openings formed in housing 109 during molding, which are configured to receive locking pins 230. Locking pins 230 of payload element 200, formed in housing 109 during molding, preferably have a flange 230a formed thereon to accommodate a "snap" or "click" type closure as will be understood. Locking pins 230 are configured to slide into and out of engagement with anchoring recesses 130, thereby locking and unlocking payload element 200 and drive element 300 of capsule 100.

Each locking pin 230 has the configuration shown in FIGS. 1 and 2 and has a resilient flange 230a disposed at a distal end of locking pin 230. Flange 230a forms an acute angle with locking pin 230. This construction permits a degree of flexion of flange 230a when suitable compressive force is applied along its transverse axis (i.e., along axis B-B shown in FIG. 2). As a result, the angle of flange 230a, which increases or decreases with such compressive force, determines the degree of frictional engagement of flange 230a with anchoring recess 130. Locking pins 230 are inserted and withdrawn from anchoring recesses 130 by flex movement of flanges 230a out of its normal configuration so that locking pin 230 are slidable into anchoring recesses 130. The resiliency of flanges 230a allows locking pins 230 to resume their original configuration when situated within anchoring recesses 130, thereby retaining locking pins 230 within anchoring recesses 130 and locking payload element 200 to drive element 300 to form an operable capsule 100.

While a click type lock is described, it should be understood that any appropriate locking means may be employed for suitably securing payload element 200 to drive element 300. Non-limiting examples of such locking mechanisms include pressure locking means, screw means, ultrasonic welding means, friction welding means, and use of adhesives such as UV curing adhesives.

Drive element 300 is attached to payload element 200 by engaging locking mechanisms 130/230 either manually or by use of specialized equipment. When drive element 300 is attached to payload element 200 a pressure force is generated in reservoir 210. This pressure collapses the weakened spots 251 as well as plugs 280 of sealed openings 250, enabling an amount of medicament stored in reservoir 210 to be displaced. The medicament is then dispensed from sealed openings 250. Semi-permanent membranes 225 allow air to enter capsule 100 from outside capsule 100, thereby allowing the medicament housed in reservoir 210 to dispense completely. It is also conceivable that reservoir 210 may be opened by special equipment required for connecting reservoir part 200 to electronics part 300, e.g. by external piercing.

It is conceivable that a two-stage seal process for containing a medicament may be employed to ensure that the medicament housed by payload element 200 does not release prior to arrival at the desired location in the gastrointestinal tract, as recognized, for example, by a programmed dosing command. A tight seal may be employed for extended storage of the medicament housed in payload element 200. Such a seal would release only upon introduction of high pressure in reservoir 210, such as that introduced when drive element 300 is attached to payload element 200. A second, weaker seal would release when the medicament housed in reservoir 210 is delivered, upon a communicated command, by a displacing piston. Accordingly, the second and weaker seal would release due to the pressure build caused by the moving piston.

It is conceived that drive element 300 and payload element 200 may be manufactured and stored separately. Drive element 300 is attached to payload element 200 to assemble capsule 100 prior to ingestion by a subject. Separate drive element 300 and payload element 200 enable decoupling of lifetime issues of the medicament housed by capsule 100 from the lifetime requirements of power source 105. Accordingly, drive element 300 is a general purpose device. Drive element 300 becomes specific when attached to payload element 300 housing a medicament. It is conceivable that attaching payload element 200 to drive element 300 may be performed by a subject or by a pharmacist using specialized equipment.

Separate components drive element 300 and payload element 200 simplify the manufacturing process of capsule 100 because drive element 300 is separate from the medicament housed by payload element 200. Thus, an electronics firm may manufacture drive element 300 and a pharmaceutical firm may manufacture payload element 200, as appropriate. Farming the manufacturing process to the appropriate area of industry resolves current issues relating to how electronic pills are filled with a medicament. Thus, sterility and other requirements relating to pharmaceutical manufacturing are met by separation of drive element 300, which may be manufactured separately from payload element 200 as it is not required that drive element 300 be introduced to a sterile pharmaceutical facility for filling.

Separate drive element 300 and payload element 200 also enable more flexible and appropriate storage options for power source 105 and the medicament(s) stored in reservoir 210. Specifically, payload element 200 can be stored in appropriate environmental conditions such as refrigeration, freezing or deep freezing or in an oxygen free atmosphere. Moreover, separate drive element 300 and payload element 200 allow sterilization of reservoir 210 of payload element 200 without risk of damaging power source 105 of drive element 300.

The action of attaching payload element 200 to drive element 300 brings capsule 100 into operational mode, e.g. by activating the electronics housed in drive element 300. The operational mode may be displayed to the subject, doctor or pharmacist by an indicating means such as a coloring mechanism, a flashing light source or a beep repeated at regular time intervals.

Figure 4:
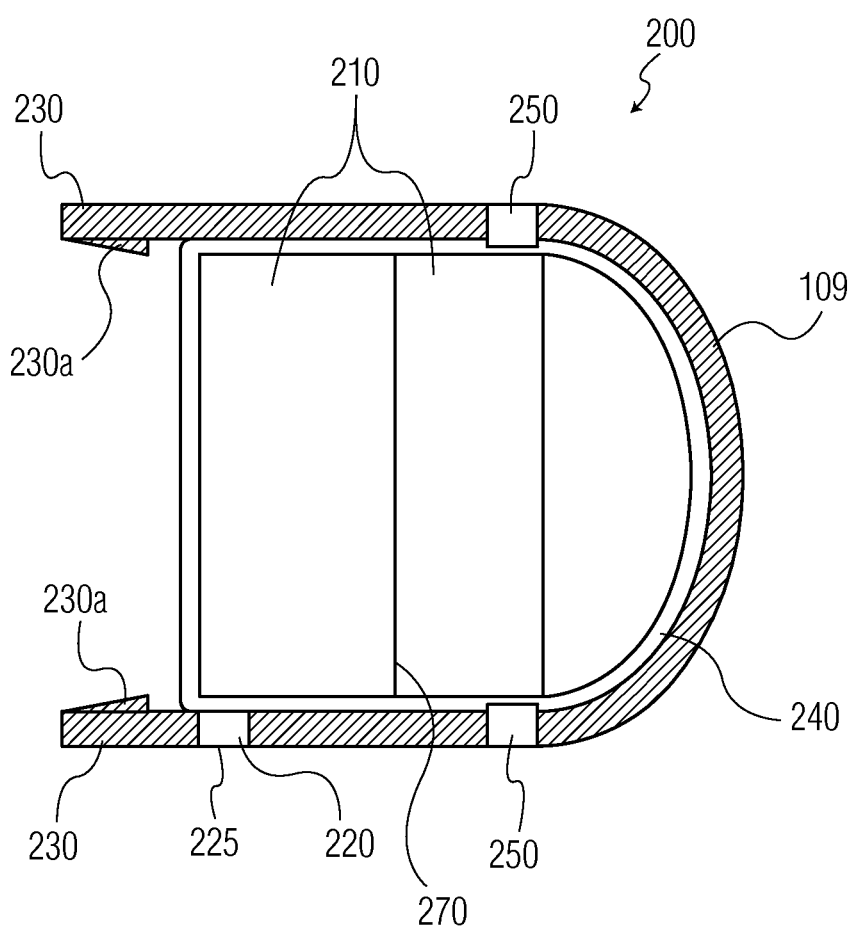
FIG. 4 is a schematic diagram showing a lateral cross-section of a payload element of an electronic capsule having two separate reservoirs in accordance with a second embodiment of the present invention.

In an alternate embodiment of the present invention illustrated in FIG. 4, payload element 200 has two or more separate reservoirs 210 for containing several medicaments. By combining several medicaments, specialized treatments may be carried out with one capsule 100. In this embodiment, reservoirs 210, each containing a medicament, are separated by a separating membrane 270.

The two or more reservoirs 210 are brought into fluid communication when payload element 200 is attached to drive element 300. Thus, the medicament becomes active when the two or more reservoir(s) 210 are brought into communication. Preferably, membrane 270 is a thin membrane which is weakened or collapsed upon assembly of capsule 100. That is, when payload element 200 is attached to drive element 300, pressure is created that opens sealed openings 250 through which the medicament is dosed. This same pressure ruptures membrane 270. A subject or pharmacist may then mix the contents of capsule 100 by shaking, vortexing or otherwise swirling electronic capsule 100. Any mixing means capable of mixing the medicaments may be employed.

In yet another embodiment of the present invention illustrated in FIG. 5, one or more separate and discrete payload elements 205, 206, each housing one or more reservoirs 210, are attached to drive element 300 to form capsule 100. This embodiment enables the subject or the pharmacist to mix differing compositions of medicaments by combining and attaching different payload elements 200 and then assembling capsule 100 prior to ingestion. The pressure generated when payload elements 205, 206 are attached ruptures gasketing insert 240 at the weakened areas 241 and 242, thereby bringing the medicament of reservoir 210 of payload element 205 into communication with the medicament of reservoir 210 of payload element 206. Alternately, gasketing insert 240 may be constructed such that reservoir(s) 210 of payload elements 205, 206 may be left intact upon attachment of payload elements 205, 206 and drive element 300 to form capsule 100 such that the different medicaments housed in payload elements 205 and 206 may be dosed sequentially.

In this embodiment, end payload element 205 housing 109 exposes one side of reservoir 210 for communication with payload element 206. Payload element 205 further has one or more openings 250 for enabling a medicament to be deposited in and dispensed from reservoir 210, a gasketing insert 240, constructed for controlled collapse at weakened areas 241 and 242 upon attachment to payload element 206, and a pair of connectors or locking mechanisms 235 for attaching end payload element 205 with payload element(s) 206. Locking mechanisms 235 are preferably a pair of locking pins. Locking pins 235, formed in housing 109 during molding, preferably have a flange 235a formed thereon to accommodate a "snap" or "click" type closure with payload element 206, as previously described. Flange 235a forms an acute angle with locking pin 235, thereby permitting a degree of flexion of flange 235a when suitable compressive force is applied.

Housing 109 of payload element(s) 206 exposes two sides of reservoir 210. Payload element(s) 206 also have a gasketing insert 240, a vent opening 220 and a semi-permeable membrane 225. Payload element(s) 206 additionally have a pair of locking mechanisms 230 for attaching to drive element 300, as previously described. Payload element(s) 206 further have a pair of connectors or locking mechanisms 236 for attaching payload element(s) 206 to end payload element 205. Locking mechanisms 236 are anchoring recesses comprising one or more openings formed in housing 109 during molding which are configured to receive locking pins 235.

In an alternate embodiment of drive element 300, illustrated in FIG. 6, a separate and discrete power source housing element 305 houses power source 105, thereby separating power source 105 from the other elements of drive element 300. This construction facilitates ready exchange of power source 105, while leaving the remaining electronic and communications components undisturbed. Power source housing element 305 has a housing 109 which contains power source 105. Housing 109 further has a pair of connectors or locking mechanisms 103 disposed therein for attaching power source housing element 305 to drive element 300. Locking mechanisms 103 are preferably anchoring recesses, as previously described. In this embodiment, drive element 300 has a housing 109 that contains a pumping device or drive unit 115 for dosing and displacing a medicament, an electrical motor support 120, a sensor platform 125 and an electronics housing 111. Electronics housing 111 houses mechanical and electrical elements necessary for operation of capsule 100. Drive element 300 housing 109 further has a pair of connectors or locking mechanism(s) 101 disposed therein for attaching drive element 300 to power source housing element 305. Locking mechanism(s) 101 are preferably locking pins, as previously described. Drive element 300 housing 109 further has a pair of connectors or locking mechanisms 130 for interaction with locking mechanism(s) 230 of payload element 200 to achieve a stable connection of drive elements 300 and power source housing element 305 to payload element 200, thereby forming an operable capsule 100. Locking mechanism(s) 130 are preferably anchoring recesses, as previously described. Prior to ingestion of capsule 100, the subject or pharmacist assembles power source housing element 305 with drive element 300 and payload element(s) 200.

It is conceivable that payload element 200 may additionally have a contactless electronically readable tag such as, for example, an RFID tag (not shown). An RFID tag, when present, functions to identify payload element 200 to drive element 300. Thus, drive element 300 may be programmed to determine whether the medicament stored in payload element 200 is what is expected. Furthermore, it is conceivable that an RFID tag may function to transfer special requirements for dosing the medicament from payload element 200 to drive element 300.

The present invention has been described with particular reference to the preferred embodiments. It should be understood that the foregoing descriptions and examples are only illustrative of the present invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

The invention claimed is:

1. An electronic capsule comprising:
  a drive element comprising:
    a drive element housing,
    control electronics for operating the electronic capsule disposed in the drive element housing,
    a drive unit disposed in the drive element housing,
    a power source operatively associated with the electronic capsule, control electronics and drive unit disposed in the drive element housing, and
    a drive element connector; and
  a payload element comprising:
    a payload element housing,
    a sealed reservoir secured in the payload element housing and storing a substance,
    one or more openings formed through the payload element housing to provide fluid communication between an inside of the payload element housing and an outside of the payload element housing for releasing the substance contained in the reservoir from the capsule, and
    a payload element connector adapted to engage the drive element connector,
  wherein an engagement of the drive element connector with the payload element connector secures the drive element to the payload element and positions the drive unit for operable communication with the reservoir, thereby making the electronic capsule operable and specific.

2. The capsule of claim 1, wherein drive element connector and the payload element connector form a click-type lock.

3. The capsule of claim 1, wherein the drive element connector is an anchoring recess.

4. The capsule of claim 1, wherein the payload element connector is a locking pin.

5. The capsule of claim 1, wherein the housing of the payload element further comprises at least one vent opening positioned to allow communication between the reservoir and the outside of the capsule.

6. The capsule of claim 5, further comprising a semipermeable membrane which overlies the vent opening and allows for air transport therethrough.

7. The capsule of claim 1, wherein the payload element further comprises a gasketing insert for providing a seal around the reservoir.

8. The capsule of claim 7, wherein the gasketing insert further has weakened areas.

9. The capsule of claim 1, wherein the payload element has two or more separate reservoirs, and wherein the separate reservoirs are each separated by a membrane.

10. The capsule of claim 9, wherein the membrane is collapsible.

11. The capsule of claim 1, further comprising a second discrete payload element having a reservoir for storing a substance, a first connector for attaching the second discrete payload to the drive element and a second connector for attaching the second discrete payload to a first discrete payload.

12. The capsule of claim 1, further comprising sensors for determining the location of the capsule.

13. The capsule of claim 1, further comprising a communication means for enabling the electronic capsule to send and receive commands.

14. The capsule of claim 1, wherein the drive element further comprises a separate and discrete power source housing element, the housing element housing the power source, thereby separating the power source from the other elements of drive element.

15. An electronic capsule comprising:
  a discrete drive element comprising:
    a drive element housing,
    control electronics for operating the electronic capsule disposed in the drive element housing,
    a drive unit disposed in the drive element housing,
    a drive element first locking mechanism, and
    a drive element second locking mechanism;
  a discrete power element comprising:
    a power element housing,
    a power source disposed in the power element housing for powering the electronic capsule and operatively associated with the control electronics and the drive unit, and
    a power element locking mechanism; and
  a discrete payload element comprising:
    a payload element housing,
    a sealed reservoir secured in the payload element housing and storing a substance,
    one or more openings in the payload element housing in fluid communication with the reservoir for releasing a substance contained in the reservoir from the capsule, and
    a payload element locking mechanism for engaging the drive element second locking mechanism,
  wherein engagement of the power element locking mechanism with the drive element first locking mechanism secures the power source housing element to the drive element, and engagement of the drive element second locking mechanism with the payload element locking mechanism secures the drive element to the payload element, said engagement making the electronic capsule operable and specific.

16. The capsule of claim 15, wherein the housing of the payload element further comprises at least one vent opening.

17. The capsule of claim 15, further comprising a communication means for enabling the electronic capsule to send and receive commands.

18. The capsule of claim 15, wherein the payload element has two or more separate reservoirs, and wherein the separate reservoirs are each separated by a collapsible membrane.

19. The capsule of claim 15, further comprising a second discrete payload element having a reservoir for storing a substance, a first locking mechanism for attaching the second discrete payload to the drive element and a second locking mechanism for attaching the second discrete payload to a first discrete payload element.

20. The capsule of claim 6, wherein the membrane impedes the flow of fluids therethrough.

21. The electronic capsule of claim 1, wherein the reservoir comprises a deformable wall.

22. The electronic capsule of claim 21, wherein the deformable wall is secured to an inside surface of the payload element housing.

23. The electronic capsule of claim 1, wherein the payload element further comprises one or more removable seals, each of the removable seals sealing one of the one or more openings.

24. The electronic capsule of claim 23, wherein the engagement of the drive element connector with the payload element connector removes the one or more removable seals from sealing engagement with the respective one of the one or more openings.

25. The electronic capsule of claim 1, wherein the reservoir comprises at least one weakened area, and wherein the engagement of the drive element connector with the payload element connector breaks the reservoir at the one or more weakened areas to create an opening in the reservoir through which the substance can exit the reservoir.

26. The electronic capsule of claim 25, wherein the at least one weakened area is aligned with at least one of the one or more openings.

\* \* \* \* \*